(12) United States Patent
Gitman

(10) Patent No.: US 9,179,975 B2
(45) Date of Patent: Nov. 10, 2015

(54) PASSING TRAY FOR SURGICAL INSTRUMENTS

(71) Applicant: SCALPAS, LLC, Wilmington, New Castle, DE (US)

(72) Inventor: Eliot Robert Gitman, Jerusalem (IL)

(73) Assignee: SCALPAS LLC, Wilmington, DE (US)

( * ) Notice: Subject to any disclaimer, the term of this patent is extended or adjusted under 35 U.S.C. 154(b) by 351 days.

(21) Appl. No.: 13/930,961

(22) Filed: Jun. 28, 2013

(65) Prior Publication Data
US 2014/0001067 A1    Jan. 2, 2014

(30) Foreign Application Priority Data
Jul. 1, 2012   (IL) .......................................... 220704

(51) Int. Cl.
*B65D 83/10*    (2006.01)
*A61B 19/02*    (2006.01)
*A61B 17/3215*  (2006.01)

(52) U.S. Cl.
CPC .......... *A61B 19/0256* (2013.01); *A61B 19/0271* (2013.01); *A61B 17/3215* (2013.01)

(58) Field of Classification Search
CPC ........... A61B 19/0271; A61B 19/0256; A61B 17/3215
USPC ........ 206/63.5, 363, 368, 370, 380, 438, 557, 206/559, 560, 565, 468; 53/473, 492; 211/60.1, 70.6, 70.7, 85.13; 220/8
See application file for complete search history.

(56) References Cited

U.S. PATENT DOCUMENTS

| 2,369,728 | A | * | 2/1945 | Farkas ........................... 206/557 |
| 4,512,466 | A |   | 4/1985 | Delang |
| 4,564,118 | A | * | 1/1986 | Heyer et al. ....................... 220/8 |
| 4,865,821 | A | * | 9/1989 | Langdon ....................... 206/370 |
| 5,083,827 | A | * | 1/1992 | Hollenbaugh, Sr. ......... 220/4.08 |
| 5,301,807 | A |   | 4/1994 | Donahue |
| 5,339,955 | A |   | 8/1994 | Horan et al. |
| 5,498,242 | A | * | 3/1996 | Cooke ........................... 206/363 |
| 6,691,884 | B1 | * | 2/2004 | Dwyer ............................. 220/8 |
| 6,821,286 | B1 | * | 11/2004 | Carranza et al. .............. 606/153 |
| 7,441,655 | B1 |   | 10/2008 | Hoftman |

(Continued)

FOREIGN PATENT DOCUMENTS

EP    2682070    1/2014

OTHER PUBLICATIONS

Extended European Search Report dated Sep. 3, 2013 for EP Application No. 13174479.9 (5 pages).

*Primary Examiner* — Luan K Bui
(74) *Attorney, Agent, or Firm* — Smith, Gambrell & Russell, LLP

(57) ABSTRACT

A passing tray for surgical instruments includes a holder having a base portion, opposing side portions open at a first end and an end portion. A sliding member having front and rear edges is slidably supported within the holder. At least one support member projects upwardly from a surface of the sliding member toward its front edge, and an actuator projects upwardly from the surface of the sliding member intermediate the front and rear edges thereof and has front and rear surfaces facing toward the front and rear edges of the sliding member, respectively. In use an elongated surgical instrument may be retained transversely between opposing surfaces of the support member and the open first end of the holder under force of the actuator.

17 Claims, 4 Drawing Sheets

(56) References Cited

U.S. PATENT DOCUMENTS

| | | |
|---|---|---|
| 2006/0042977 A1 | 3/2006 | Sandel |
| 2008/0300612 A1* | 12/2008 | Riza et al. ............... 206/363 |
| 2010/0252467 A1* | 10/2010 | Cote et al. .............. 206/363 |
| 2013/0256167 A1* | 10/2013 | Scott et al. ............. 206/370 |

* cited by examiner

PASSING TRAY FOR SURGICAL INSTRUMENTS

FIELD OF THE INVENTION

This invention relates to passing trays used to pass surgical instruments between medical staff during surgical procedures.

BACKGROUND OF THE INVENTION

It is well recognized that a major, if not the major, cause of injury to medical staff during surgical procedures is the infelicitous handling of sharp surgical instruments such as scalpels, scissors and the like. It is estimated that scalpel injuries account for between 7% and 12% of all sharps injuries. This statistic has spawned significant effort in improving the safety of surgical instruments. One result of this effort is the so-called "safety scalpel", whose blade is retractable thus allowing ancillary staff to pass it to the surgeon in its retracted state. In theory this ought to prove an ideal solution. However, in practice it has been shown not to be because in the pressure of an operation and the rapid transfer of surgical instruments to and fro between ancillary staff and the surgeon, the blade is apt not to be fully retracted. A surgeon grasping the scalpel while concentrating more on the health of the patient than his or her own welfare is prone to injury. Indeed, the a priori assumption on the part of the surgeon that the scalpel blade is retracted may lead to less caution than if it were known that the blade was exposed.

The inventor has been informed that even in the same hospital there is no one consistent method of passing scalpels and the like between operating room staff. While one surgeon reported that he has the scalpel passed to him by hand with the handle pointing in his direction, so as not to get cut by mistake from fumbling, a second surgeon has the scalpel passed to him in the opposite direction for fear or cutting the assistant. Such mutually contradictory procedures are confusing to the ancillary staff and are prone to increase the risk of injury.

It has thus been concluded that a hands-free passing technique using a scalpel holder is a safer alternative to the safety scalpel.

U.S. Pat. No. 5,301,807 discloses such a holder that is used during surgical procedures and to dispose of scalpels after use. A number of scalpels are held in separated positions to be easily grasped when needed. The holder includes a cover for the blade ends of the scalpels, and a retractable cover for the handle ends. Each scalpel rests readily gripped on edge in its individual compartment. Adhesive pads-are optionally used to secure the holder in fixed location on an instrument tray during the operation.

U.S. Pat. No. 7,441,655 discloses a dual function transfer tray that can be used for either a scalpel or a suturing needle holder with suturing needle. A scalpel slot is formed in the bottom of a relatively deep set of sloped walls. A suture needle cavity is formed above the first slot. At a mid-section of the scalpel slot and the half-cylindrical suture needle cavity are opposing and deep V-shaped cutaway sections in the sidewalls with a flat floor section between them.

SUMMARY OF THE INVENTION

According to the invention there is provided a passing tray for surgical instruments, said passing tray comprising:

a holder having a base portion supporting mutually opposing side portions open at a first end and an end portion abutting said side portions at a second end thereof opposite the first end, a sliding member having a front edge and a rear edge and being slidably supported within the holder such that in a retracted position the front edge of the sliding member is aligned with the first end of the holder, at least one support member projecting upwardly from a surface of the sliding member toward the front edge thereof, and an actuator projecting upwardly from said surface of the sliding member intermediate the front and rear edges thereof, the actuator having a front surface facing toward the front edge of the sliding member and having a rear surface facing toward the rear edge of the sliding member;

whereby in use an elongated surgical instrument may be retained transversely between opposing surfaces of the support member and the open first end of the holder under force of the actuator for urging the support member toward the holder.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
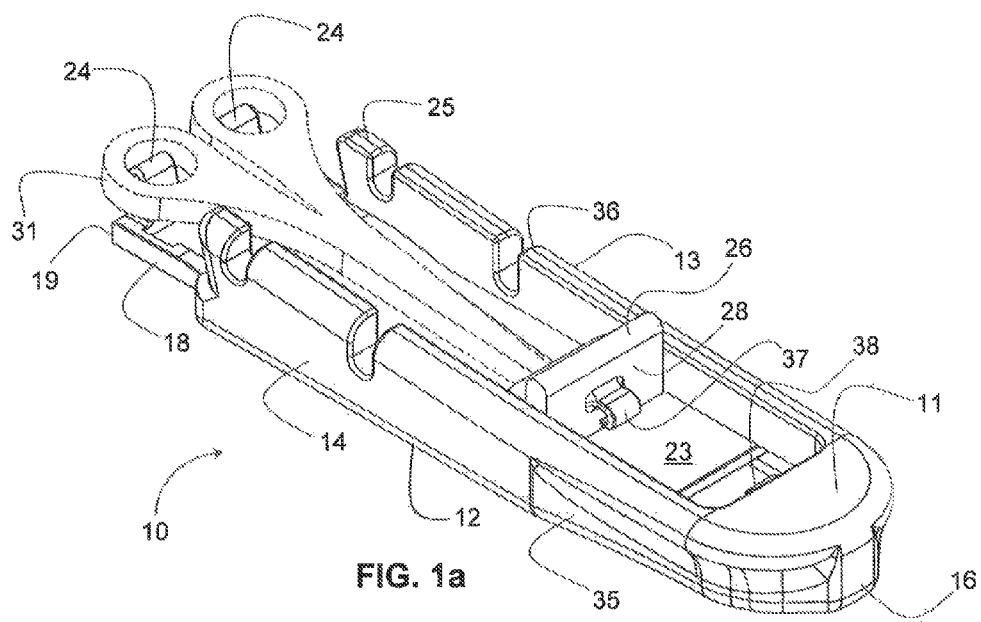
FIGS. 1a, 1b and 1c show respectively a perspective view, and plan and side elevations of a passing tray according to an embodiment of the invention.

In the following description of some embodiments, identical components that appear in more than one figure or that share similar functionality will be referenced by identical reference symbols.

Referring to the figures there is shown a passing tray 10 for surgical instruments. The passing tray 10 comprises a holder 11 having a base portion 12 supporting mutually opposing side portions 13, 14 open at a first end 15 and an end portion 16 abutting the side portions at a second end 17 thereof opposite the first end. A sliding member 18 having a front edge 19 and a rear edge 20 is slidably supported within opposing grooves 21 formed in the side portions such that in a retracted position (i.e. when the tray is fully inserted) the front edge of the sliding member is aligned with the first end of the holder. At least one support member 22 projects upwardly from a surface 23 of the sliding member 18 toward the front edge thereof. As shown in the figures the support member 22 is dimensioned so that an upper lip 24 thereof is slightly lower than opposing upper rims 25 of the side portions. Nevertheless, the upper lip 24 extends higher than the base 23 of the sliding member such that a surgical instrument supported longitudinally by the support member 22 slants downward with its center of gravity well inside the sliding member 18. In other embodiments the support member 22 may be dimensioned so that an upper lip 24 thereof is level with or extends beyond opposing upper rims 25 of the side portions.

An actuator 26 projects upwardly from the surface of the tray member intermediate the front and rear edges thereof, and has a front surface 27 facing toward the front edge 19 of the tray member and a rear surface 28 facing toward the rear edge 20 thereof. The actuator 26 is shown as a plate, the front surface 27 of which optionally supports a retaining portion 29 at a height slightly proud of the exposed upper surface of the sliding member 18, so as to provide a clearance 30. The clearance 30 accommodates the sharp tip of a surgical instrument placed longitudinally on the tray with its handles supported by the support member 22 and prevents the instrument from dislodging inadvertently during transfer between hospital personnel.

Figure 1B:
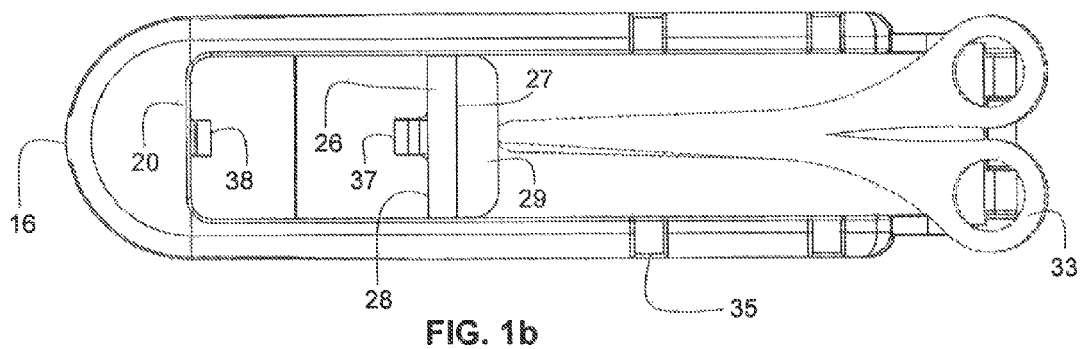
Figure 1C:
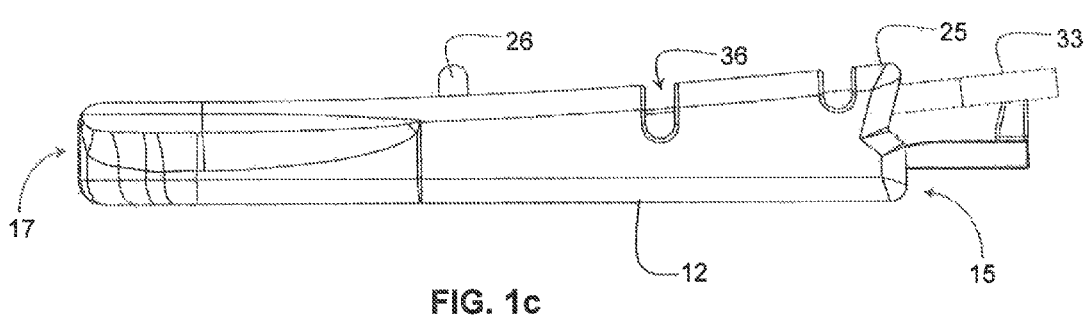
Figure 2A:
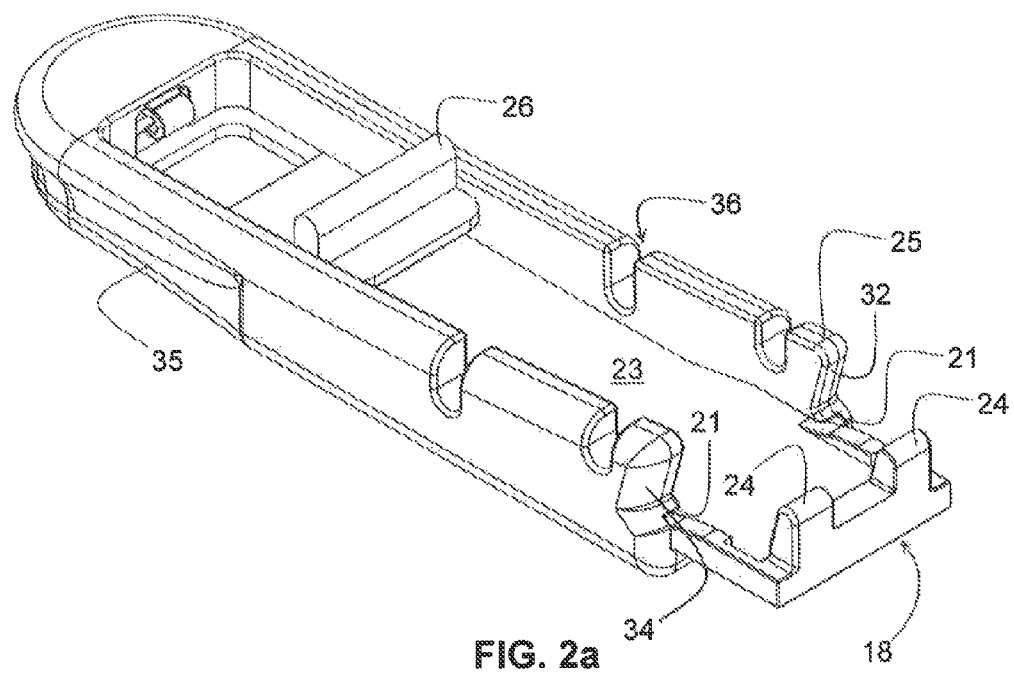
FIGS. 2a and 2b are perspective views of the passing tray showing a surgical knife supported transversely by the tray.
Figure 2B:
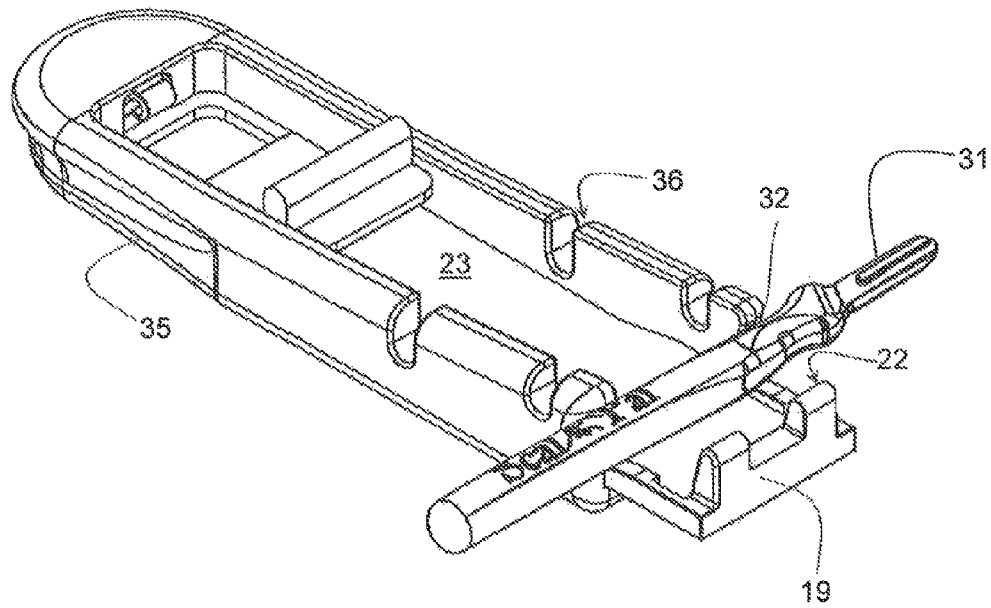
Figure 2C:
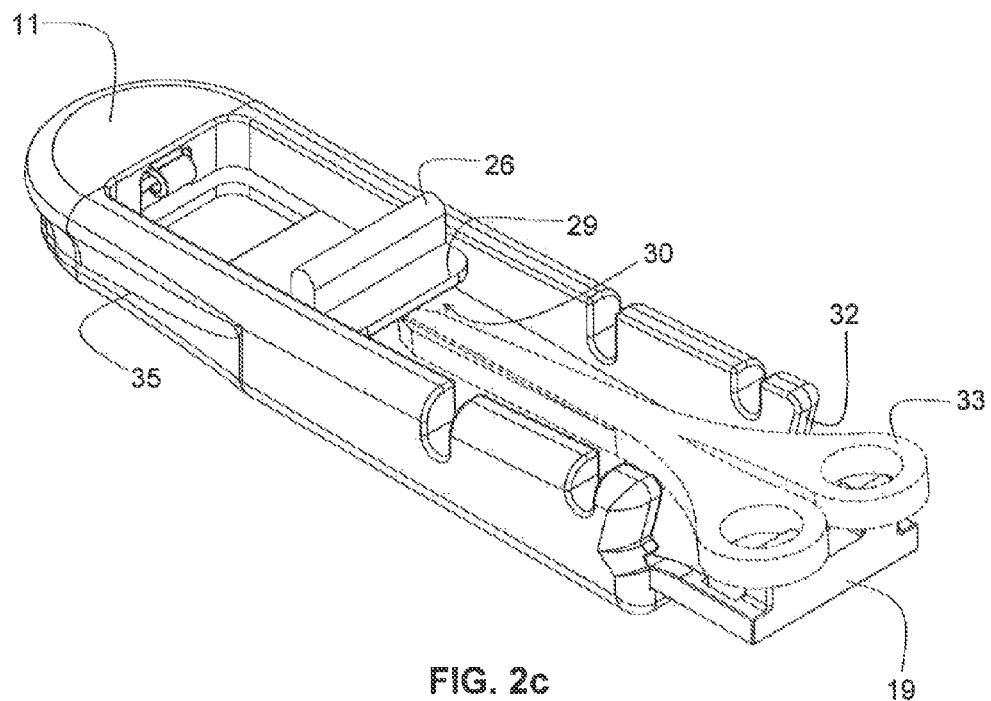
FIG. 2c is a perspective view of the passing tray showing a pair of surgical scissors supported longitudinally by the tray.
Figure 3A:
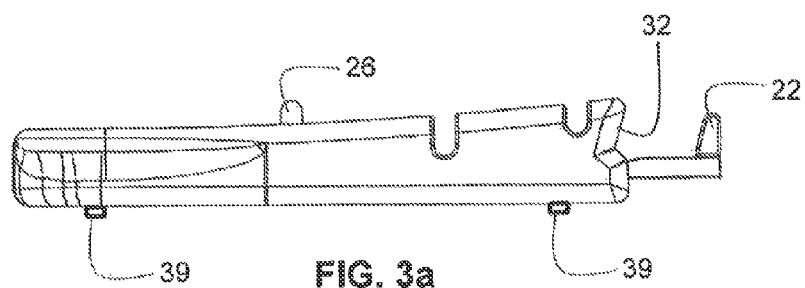
FIGS. 3a and 3b are side elevations of the passing tray showing a surgical instrument supported longitudinally by the tray.
Figure 3B:
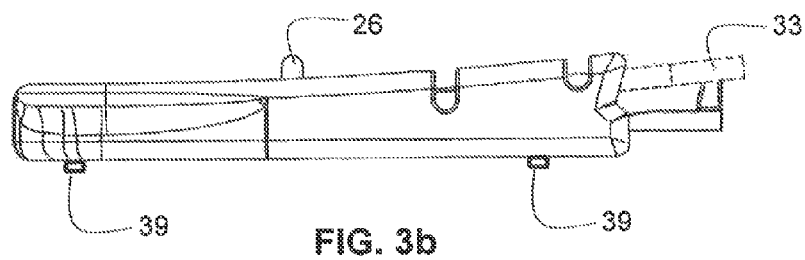

In use an elongated surgical instrument such as a surgical scalpel 31 may be supported on the tray transversely as shown in FIG. 2b between the support member 22 and the open first end 15 of the holder. When used in this manner, the surgical instrument is retained between the inner surface of the support members 22 and opposing outer surfaces of the upright front edges 32 of the holder 11. Alternatively, as shown in FIGS. 1a, 1b, 1c and 2c. an elongated surgical instrument such as a pair of surgical scissors 33 is supported longitudinally along the tray member with a handle of the surgical instrument supported by the upwardly extending lips 24 of the support member 22 and a sharp end of the surgical instrument being retained by the retaining portion as explained above. it should be noted that while FIG. 2b shows a surgical scalpel and FIGS. 1b, 1c and 2c show a pair of surgical scissors, this is merely by way of example and not limitation. Other tools may be passed and all tools may be retained transversely and depending on the type of tool may typically also be conveyed longitudinally. When the tool is conveyed longitudinally, the sharp end of the tool is secured between the surface 23 of the sliding member 18 and the retaining portion 29, enabling the surgeon or ancillary to grip the tool by its opposite blunt end or handle. The retaining portion 29 plays no part in the transverse retention of tools between the support member 22 and the upright front edges 32 of the holder 11.

The front edge 32 of each of the side portions 13, 14 may be provided with a concave depression 34 for accommodating a surface of the tool 31 and impeding accidental dislocation thereof when the actuator 26 is closed. Likewise, an internal surface of the support member 22 may be provided with a convex shape complementary to the concave depression 34 so as to form inclined parallel surfaces for supporting a planar tool therebetween at a slight inclination to the vertical. This facilitates removal of the tool in a generally arcuate motion upward and away from the passing tray.

Preferably, the second end 17 is shaped for comfortable manual gripping. This may be accomplished by providing the side portions 13, 14 with a beveled edge 35 toward the second end 17 of the holder. One or more pairs of coaxial slots or grooves 36 is formed in opposing upper rims of the side portions 13, 14, each pair dimensioned for accommodating a respective surgical instrument disposed transversely therein.

The actuator 26 is adapted for resilient biasing toward the rear edge 20 of the holder so as to exert pressure on a surgical instrument held transversely between the front edge 19 and the support members 22. To this end, a first hook 37 may be formed on the rear surface 28 of the actuator and a second hook 38 may be formed on an internal surface of the end portion 16 for supporting a rubber band (not shown) therebetween. The rubber band constitutes a resilient bias and is preferably formed of a type of rubber that may be autoclaved so as to be suitable for repeated use. Obviously, the desired bias force may be achieved using other resilient bias means, such as a spring.

In both FIGS. 2b and 2c, the tool is retained either between the mating surfaces of the support member 22 and the upright front edges 32 of the holder 11 or by the support member 22 and the retaining portion 29. Consequently, the tool may be passed with the passing tray in any desired orientation, unlike known devices which must be maintained horizontal to prevent the tool from falling out. Withdrawing the tool overcomes the bias force of the rubber band or spring. if necessary, particularly when passing a heavier tool, the bias force may be supplemented with slight finger pressure applied by the ancillary passing the tool to the surgeon. In either case, the orientation of the blade is not critical since it can be handled by either a left- or right-handed surgeon without the need to approach the sharp end and after use it may likewise be returned to the passing tray by the surgeon in a reverse motion so as to be gripped by the support member 22 and retained under the resilient bias of the actuator 26.

Figure 4A:
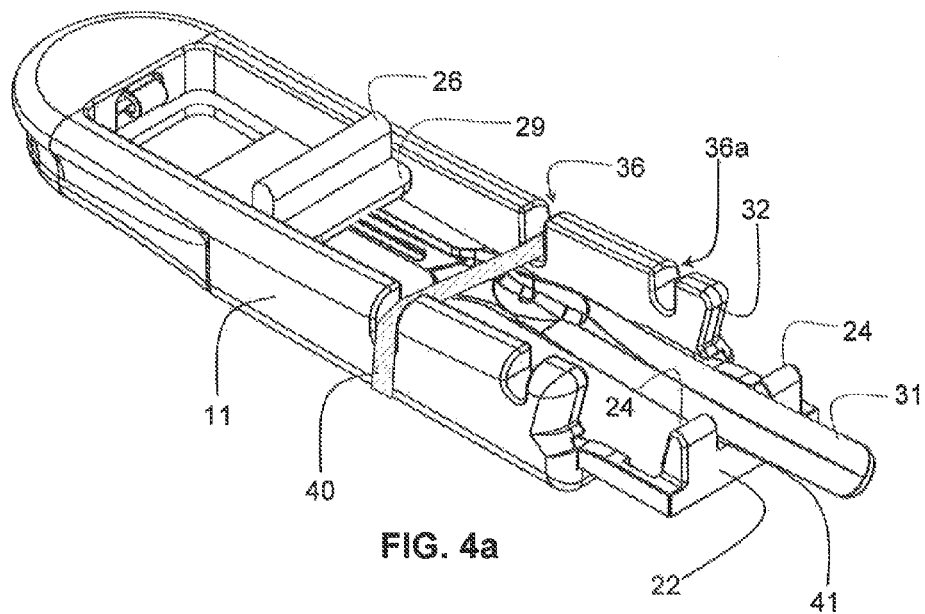
FIG. 4a is a perspective view of the passing tray showing a surgical instrument supported longitudinally and having a retention mechanism for retaining the instrument and facilitating removal.

One or more friction grips such as rubber pads 39 may be provided on the base portion 12 for impeding sliding of the passing tray along a surface on which the passing tray is disposed. The friction grips may simply include one or more rubber bands 40 wrapped around the holder 11 as shown in FIG. 4a so as to encircle the opposing side portions 13, 14 thereof. In FIG. 4a the rubber bands are accommodated within the opposing slots or grooves 36 in the upper rims of the side portions 13, 14 for reasons that are described in further detail below. But so far as their use as friction grips is concerned, they may encircle the holder intermediate the grooves 36. Again, the rubber bands 40 are preferably formed of a type of rubber that may be autoclaved so as to be suitable for repeated use.

The support member 22 may be a unitary support or, as shown in the figures, may be a pair of support members 22 dimensioned for accommodating respective handles of a pair of surgical scissors 33.

Preferably, the support member 22 is configured for retaining an edge of a sleeve of a safety scalpel held longitudinally in the holder. When a surgeon grips the handle of the scalpel and draws it away from the holder, the sleeve is then retained by the support member 22 as the safety scalpel is withdrawn, thereby rendering the scalpel ready for use without prior need to remove the safety sleeve.

In use, an ancillary prepares one or more surgical instruments in a preparation area of the operating theater. In the examples shown in the figures, a surgical scalpel is retained transversely or a pair of scissors is disposed longitudinally with the sharp tip retained by the retaining portion 29. More generally, the sliding member 18 is extracted slightly and a scalpel 32 is placed in the ensuing gap between the front edge of the holder and the projecting support member 22. The rear edge of the support member 22 urges against the surgical instrument under the resilient bias afforded by the rubber band or a spring articulated to the actuator 26. By such means, the surgical instrument is held securely during the act of passing the tray toward the surgeon, who is able to take the surgical instrument via its handle without risk of injury to himself or to the ancillary. The surgical instrument may be easily withdrawn by a simple upward movement, since the pressure exerted by the resilient bias while sufficient to prevent unintentional dislocation of the surgical instrument does not obstruct or impede its intentional removal. If desired, the ancillary may grip the holder via the beveled edge 33 between the thumb, middle finger and the pinky, leaving the forefinger free to push the actuator forward during the act of handing the tray to the surgeon, thereby even further facilitating removal of the surgical instrument. Likewise, when the surgeon wishes to pass the used surgical instrument back to the ancillary, the ancillary presses on the actuator 26 so as provide sufficient clearance between the front edge of the holder and the projecting support member 22 for accommodating the tool. Releasing pressure on the actuator 26 causes it to spring back under the resilient biasing force of the rubber band or spring thereby preventing the surgical instrument falling during its transfer from the operating table back to the preparation area.

FIG. 4*a* is a perspective view of the passing tray 10 showing a surgical instrument 31 supported longitudinally and having a rubber band 40 secured within the grooves 36. The upwardly extending lips 24 of the support member 22 define an intermediate gap 41 having a lower edge that supports the handle of the surgical instrument, the sharp end of which is supported on the upper surface 23 of the sliding member 18 under the retaining portion 29. Since the lower edge of the gap 41 is higher than the surface 23 of the sliding member 18, the instrument 31 maintains a downward inclination from the handle to the sharp end thereof. The internal height and location of the grooves 36 are such that when the instrument is thus inserted it is frictionally retained by the rubber band 40, which thus operates as a retention mechanism since it retains the instrument regardless of its size. Thus, short instruments that are shorter than the length of the sliding member 18 can be laid on the surface 23 of the sliding member 18 and retained by the rubber band 40 as can long instruments whose handles project through the gap 41 and can thus be gripped easily when it is required to remove them from the passing tray. Alternatively, short instruments that can be retained with their handles projecting through the gap 41 and retained by a rubber band 41 located in a groove 36*a* closer to the support member 22. In such case, the depth of the rear groove 36*a* must be sufficient that the rubber band 40 is low enough to exert frictional contact with the instrument.

However, a particular benefit of the retention mechanism comes into play for instruments that are long enough to be supported in the gap 41 while not being so long as to project therethrough and are therefore not amenable to being gripped. Operation of the retention mechanism in this condition will now be explained with reference to FIGS. 4*b* to 4*d*.

Figure 4B:
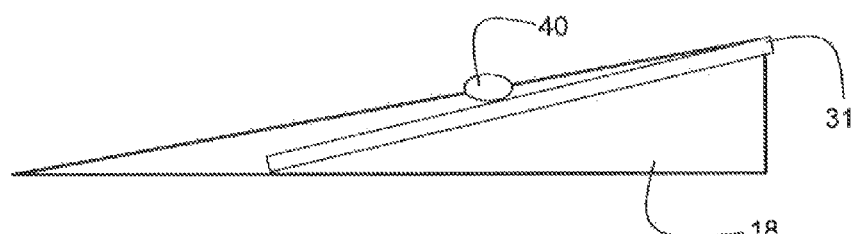
FIGS. 4b to 4d are schematic representations of a partial side elevation of the passing tray shown in FIG. 4a useful for explaining its operation.
Figure 4C:
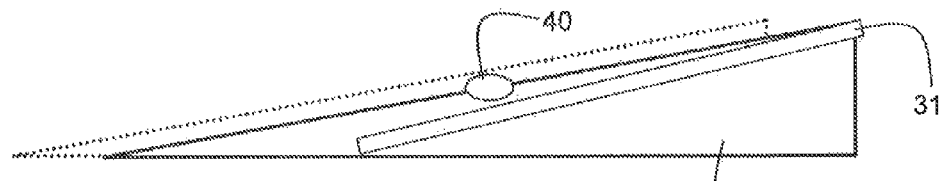

FIG. 4*b* depicts schematically the closed (i.e. storage) position of the instrument, where the actuator 26 is pulled by the resilient bias so that the sliding member 18 and the retaining portion 29 are located as far back as possible to the rear of the holder 11. As explained, in this position the sharp tip of the instrument is located underneath the retaining portion 29 and the far extremity of its handle is supported between the gap 41 of the support member 22 leaving minimal or at least insufficient projection to allow for easy handling. When the actuator 26 is now drawn toward the front of the holder, the instrument is drawn forward together with the sliding member 18. Since the sliding member 18 now projects forward of the front edges 32 of the holder 11, so also does the instrument 31 extend beyond the front edges 32 of the holder 11 even though it remains within the boundary of the sliding member 18. Owing to the downward inclination of the instrument frictional contact with the rubber band becomes diminished, and there may even come a point where it is lost as depicted in FIG. 4*c* such that further rearward motion of the sliding member simply drags the instrument with it. When the actuator 26 is now released, it springs back under the force of the resilient bias carrying the instrument in the reverse direction. Again, owing to the downward inclination of the instrument frictional contact with the rubber band now increases.

Figure 4D:
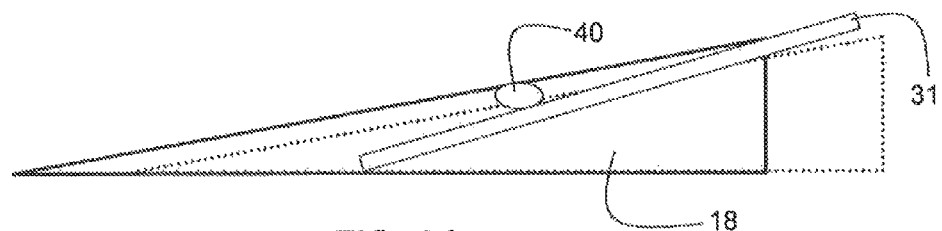

FIG. 4*d* depicts the extreme condition where lost frictional contact is re-established. But regardless of whether or not frictional contact were previously lost, the increased frictional contact between the instrument 31 and the rubber band 40 arrests the instrument and prevents it from moving back with the sliding member 18. As a result, the frictional contact between the rubber band 40 and the instrument 31 exceeds any marginal frictional contact between the sliding member 18 and the sharp end of the instrument. This occurs when the handle still extends beyond the front edges 32 of the holder 11. Consequently, as the sliding member 18 continues in its rearward travel into the holder from a most extended position shown in dotted outline to a fully withdrawn position shown in full outline, the handle of the instrument remains exposed and projects outward through the gap of the support member and is easily removed.

It will be appreciated that while several embodiments have been described, the description is not intended to be limiting and the passing tray may be used for other tools and in other ways than those described.

For example, instruments having an elongated handle supporting sharp tools at both ends may also be safely retain transversely for easy removal via their handles.

Likewise, scissors whose handles cannot be simultaneously accommodated by the two upwardly extending lips 24 of the support member 22 may be retained by a single handle only. Alternatively, they may be retained with their handles astride the extending lips 24.

It should also be noted that while reference has been made to rubber bands they do not need to be made of rubber. Any elastic bands may be used provided that they are formed of a resilient material capable of exerting a frictional grip on contact with an instrument.

The invention claimed is:

1. A passing tray for surgical instruments, said passing tray comprising:
   a holder having a base portion supporting mutually opposing side portions open at a first end and an end portion abutting said side portions at a second end thereof opposite the first end,
   a sliding member having a front edge and a rear edge and being slidably supported within the holder such that in a retracted position the front edge of the sliding member is aligned with the first end of the holder,
   at least one support member projecting upwardly from a surface of the sliding member toward the front edge thereof, and
   an actuator projecting upwardly from said surface of the sliding member intermediate the front and rear edges thereof, the actuator having a front surface facing toward the front edge of the sliding member and having a rear surface facing toward the rear edge of the sliding member;
   whereby in use an elongated surgical instrument may be retained transversely between opposing surfaces of the support member and the open first end of the holder under force of the actuator for urging the support member toward the holder.

2. The passing tray according to claim 1, including a retaining portion projecting from the front surface of the actuator at a height that provides clearance with the surface of the sliding member;
   whereby the elongated surgical instrument may be retained longitudinally along the sliding member with a handle of the surgical instrument supported by the at least one support member and a sharp end of the surgical instrument being retained between the retaining portion and the surface of the sliding member.

3. The passing tray according to claim 1, wherein the second end is shaped for comfortable manual gripping.

4. The passing tray according to claim 3, wherein the side portions have a beveled edge toward the second end of the holder.

5. The passing tray according to claim 1, including at least one pair of coaxial slots or grooves formed in opposing upper rims of the side portions and dimensioned for accommodating a surgical instrument disposed transversely therein.

6. The passing tray according to claim 1, wherein the actuator is adapted for resilient biasing toward the rear edge of the holder so as to exert pressure on a surgical instrument held transversely between the front edge and the at least one support member.

7. The passing tray according to claim 6, including a first hook formed on the rear surface of the actuator and a second hook formed on an internal surface of the end portion for supporting a resilient bias therebetween.

8. The passing tray according to claim 7, wherein the resilient bias is a rubber band formed of a type of rubber that may be autoclaved so as to be suitable for repeated use.

9. The passing tray according to claim 1, further including one or more friction grips on the base portion for impeding sliding of the passing tray along a surface on which the passing tray is disposed.

10. The passing tray according to claim 9, wherein the friction grips include one or more rubber bands wrapped around the holder so as to encircle the opposing side portions thereof.

11. The passing tray according to claim 1, including a pair of support members dimensioned for accommodating respective handles of a pair of surgical scissors.

12. The passing tray according to claim 1, wherein the at least one support member is configured for retaining an edge of a sleeve of a safety scalpel or hypodermic syringe held longitudinally in the holder, thereby removing the sleeve as the safety scalpel or hypodermic syringe is withdrawn by sliding along the support member.

13. The passing tray according to claim 1, wherein the at least one support member is dimensioned so that an upper lip thereof is level with or extends beyond opposing upper rims of the side portions.

14. The passing tray according to claim 1, wherein a front edge of each of the side portions is provided with a concave depression for accommodating a surface of the tool and impeding accidental dislocation thereof when the actuator is closed.

15. The passing tray according to claim 14, wherein an internal surface of the support member has a convex shape complementary to the concave depression for supporting a planar tool at a slight inclination that facilitates removal of the tool in a generally arcuate motion upward and away from the passing tray in either direction.

16. The passing tray according to claim 1, including at least one pair of coaxial slots or grooves formed in opposing upper rims of the side portions and dimensioned for accommodating an elastic band therein so as to frictionally grip an instrument disposed longitudinally in the passing tray.

17. A method for removing an instrument from the passing tray according to claim 16 where the instrument is retained longitudinally and is dimensioned such that an insufficient length of a handle of the instrument projects beyond the support member for easy gripping by a user, the method comprising:

storing the instrument with an end of its handle resting on a gap between spatially separated lips projecting upwardly from the support member and with a sharp end of the instrument being supported on the sliding tray so that the instrument is inclined downward from the end of the handle toward the sharp end;

pushing the actuator against the resilient bias so that the sliding member moves forward beyond the front of the holder carrying the instrument with it whereby the end of the handle projects beyond the support member and the instrument contacts the elastic band and is subjected to frictional contact force thereby; and releasing the actuator so as to be pulled back by the resilient bias thereby retracting the sliding tray into the holder while retaining the instrument by the frictional contact force of the elastic band against the backward pull of the sliding tray such that the end of the handle remains projecting beyond the support member and is easily gripped.

* * * * *